(12) United States Patent
Foroni

(10) Patent No.: US 7,213,312 B2
(45) Date of Patent: May 8, 2007

(54) FUNERARY CONTAINER MADE OF PAPER MATERIAL, AND ASSEMBLY DEVICE EMPLOYED THEREIN

(76) Inventor: Ida Foroni, Via Carnia, 138, 21100 Varese (IT)

( * ) Notice: Subject to any disclaimer, the term of this patent is extended or adjusted under 35 U.S.C. 154(b) by 287 days.

(21) Appl. No.: 10/343,739

(22) PCT Filed: Jul. 30, 2001

(86) PCT No.: PCT/IT01/00416

§ 371 (c)(1),
(2), (4) Date: Jul. 25, 2003

(87) PCT Pub. No.: WO02/11660

PCT Pub. Date: Feb. 14, 2002

(65) Prior Publication Data

US 2004/0098847 A1    May 27, 2004

(30) Foreign Application Priority Data

Aug. 4, 2000   (IT) .......................... MI2000A1823

(51) Int. Cl.
*A61G 17/00* (2006.01)

(52) U.S. Cl. ........................... 27/4; 27/27; 229/117.09; 229/117.19; 16/424; 16/425; 220/759

(58) Field of Classification Search ..................... 27/2, 27/4, 27; 16/424, 425; 220/759, 770, 772; 229/117.09, 117.19, 125.37, 125.39, 181, 229/189, 198

See application file for complete search history.

(56) References Cited

U.S. PATENT DOCUMENTS

| | | | | |
|---|---|---|---|---|
| 520,015 A * | 5/1894 | Bannister | .................... | 16/424 |
| 626,432 A * | 6/1899 | Kircher | .................... | 16/424 |
| 2,494,473 A * | 1/1950 | Dowling | .................... | 27/3 |
| 2,723,073 A * | 11/1955 | Fellowes | .................... | 229/166 |
| 2,992,768 A * | 7/1961 | Gatward | .................... | 383/21 |
| 3,220,080 A | 11/1965 | Connelly | | |
| 3,367,004 A * | 2/1968 | Schneider | .................... | 27/3 |
| 3,900,157 A * | 8/1975 | Roth | .................... | 206/737 |
| 5,623,752 A | 4/1997 | Gillard et al. | | |
| 5,823,424 A * | 10/1998 | Allen | .................... | 229/120.07 |
| 6,006,984 A * | 12/1999 | Chung et al. | .................... | 229/137 |
| 6,039,243 A * | 3/2000 | Lickton | .................... | 229/117.01 |
| 2004/0104264 A1* | 6/2004 | Meeker | .................... | 229/117.19 |

FOREIGN PATENT DOCUMENTS

| | | |
|---|---|---|
| AU | 399 705 B | 7/1995 |
| FR | 1 569 802 | 6/1969 |
| GB | 2 236 141 A * | 3/1991 |
| WO | WO 91/04421 A | 4/1991 |
| WO | WO 95/08973 A | 4/1995 |

* cited by examiner

*Primary Examiner*—William L. Miller
(74) *Attorney, Agent, or Firm*—Pearne & Gordon LLP

(57) ABSTRACT

A funerary container made of paper material comprises a predetermined number of laminar elements (2) flexibly connected to each other and defining in mutual cooperation a housing box (3) destined to contain a body and having at least a bottom wall, a plurality of lateral wall and at least a closure portion; the container further comprises a predetermined number of assembly devices (4), whereof each is operatively active on at least two laminar elements (2) to maintain them in a mutually approach position in operative conditions. At least one of the assembly devices (4) comprises at least a main fastening element (5) irremovably connected to a first laminar element (2a) and destined to receive in coupling fashion at least a second laminar element (2b). The assembly device (4) further comprises a complementary fastening element (6) operatively active on the second laminar element (2b) in operative conditions and destined to engage at least partially with the main fastening element (5).

20 Claims, 4 Drawing Sheets

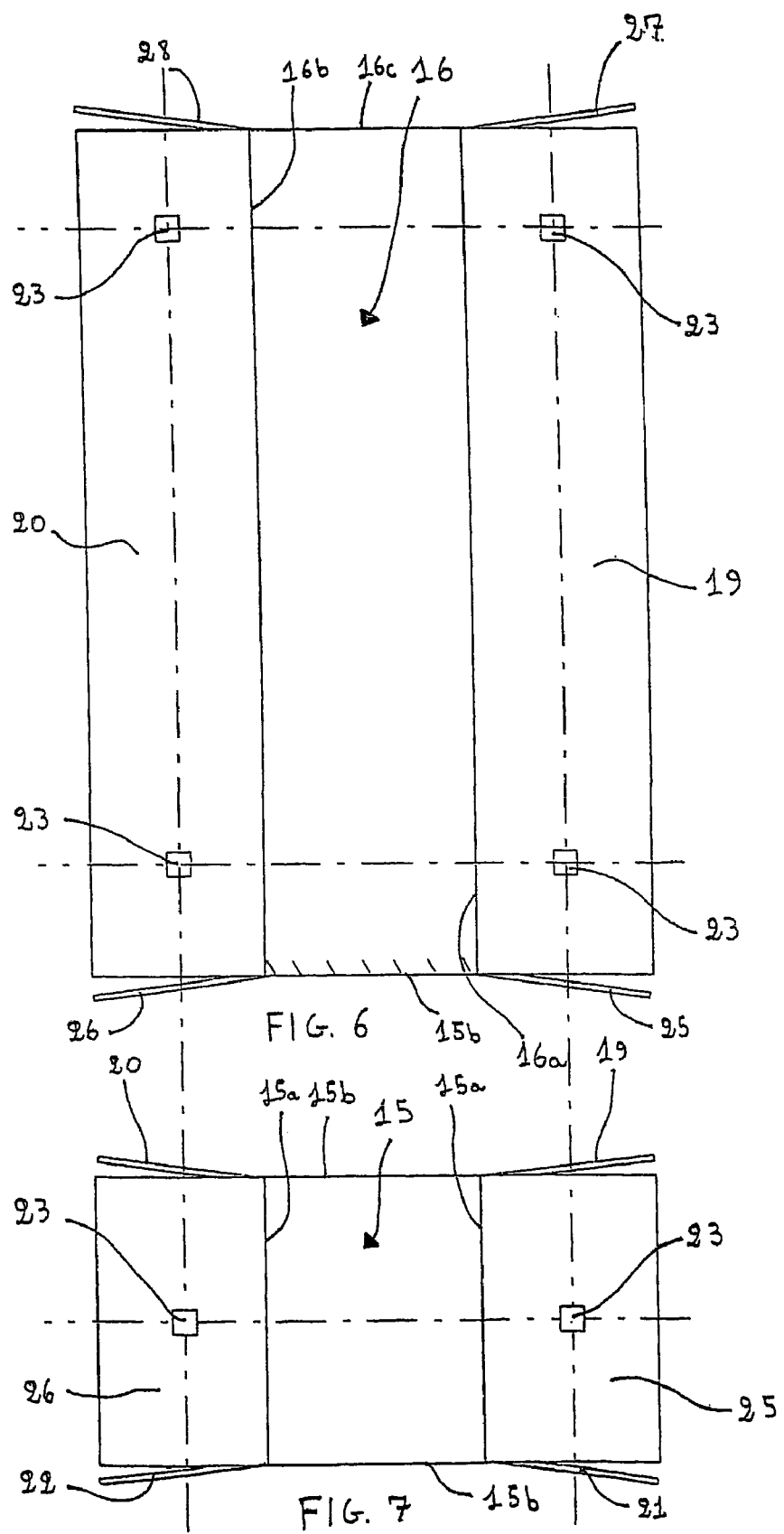

FUNERARY CONTAINER MADE OF PAPER MATERIAL, AND ASSEMBLY DEVICE EMPLOYED THEREIN

This application claims the benefit of International Application Number PCT/IT01/00416, which was published in English on Feb. 14, 2002.

The present invention relates to a funerary container made of paper material, as well as an assembly device employed therein.

As is well known, in different situations or for disparate incidental and/or ethical reasons it is preferable to employ containers for human corpses made of light material, instead of employing traditional but heavy containers made of wood or metal.

In general, in such cases coffins are readied whose walls are constituted essentially by paper material; such paper material is, in nearly all cases, constituted by one or more layers of cardboard superposed and so arranged as to define a containment body of substantially prismatic shape. It should be noted that such containers can often be assembled at the time they are needed, since the different sides constituting the containment body are generally obtained starting from a single sheet of cardboard, die cut according to a polygon corresponding to the two-dimensional development of the faces of the prismatic body itself.

By acting appropriately on folding lines (positioned in correspondence with the corners of the prismatic body), one easily obtains the complete shape of the funerary container; naturally, once the different sides of the container are adequately oriented, its shape needs to be locked, by appropriately securing the sides.

The operations for mutually securing the cardboard sides can be carried out by employing appropriate devices, which act by mutually securing at least two cardboard walls.

Generally, adhesive surfaces can be employed, or use can be made of fastening elements of more or less complex nature, depending on the area in which they are installed (for instance, they can be simple screw and nut couplings or reinforcing ribs that locally circumscribe a vertex of the container). In addition, the presence can also be provided of coupling tabs able to be extracted from the cardboard panels and destined to be coupled in corresponding seats on another panel.

It is also common, in the field of funerary containers made of paper material, to use stiffening frames (typically made of wood), which are positioned in such a way as to be integral with the actual container and to withstand the loads deriving from the weight of a corpse without causing the deformation or even the breakage of the cardboard.

The prior art summarily described above, however, has some limitations.

First of all, known assembly system have, in each of the described variations, some drawbacks relating to their operative flexibility and practicality of use.

Generalising the above observations, note that known assembly systems require a rather long period of time to be readied, or make it necessary to employ tools (which are not always easy to use or find, considering possible scenarios of employment of such funerary containers); in addition, it must also be noted that oftentimes "tab" couplings do not offer sufficient guarantees of structural strength, with evident disadvantages in terms of the reliability of the container itself.

One drawback associated to what is discussed above is given by the fact that the peculiar difficulties of employment of known assembly systems often entail the need to have specialised operators available, which once again detracts from operative flexibility and ease of use.

Moreover, it should be noted that the presence of stiffening frames greatly decreases the practicality of funerary containers made of paper material, since the frames themselves are difficult to fold or stow in small spaces; alternatively, they need to be dismantled and separated from the cardboard elements, and hence have to be mounted back onto them when the container is to be used; this leads to additional problems of impracticality of use and often requires the presence of specialised operators and/or dedicated tools for the assembly operation.

Yet a further drawback linked to known funerary containers resides in the fact that the presence of the stiffening frame entails a non negligible increase in production costs; the frame, usually made of wooden material or also of plastic material, causes considerable environmental impact problems, especially in those cases in which it is made of non biodegradable material and if the funerary container needs to be subjected to cremation or buried for a long period of time.

In this situation the technical task constituting the basis for the present invention is to devise a funerary container made of paper material that is able substantially to overcome the aforementioned limitations. Within the scope of said technical task, an important aim of the invention is to devise a funerary container whose production and assembly are significantly simple and rapid.

An additional aim at the base of the present invention consists of devising a funerary container that is free from the need to have a stiffening frame, even when it has to contain particularly heavy and/or large bodies. Obviously, the present invention aims to achieve the optimal coexistence, in a funerary container made of paper material, of high performance in terms of admissible load and of easy disassembly and reduced storage space and reduced environmental impact, especially in the cases in which the container (and consequently its content) are destroyed by cremation. Yet another aim of the present invention is to provide an assembly device, particularly suitable to be installed on funerary containers made of plastic material, allowing their storage in disassembled form while also allowing a rapid assembly.

An additional aim of the present invention is to provide an assembly device, in particular employed in funerary containers made of paper material, which offers a particularly stable coupling and is easy to deploy, even by non specialised operators.

Lastly, another aim of the present invention is to devise a funerary container made of paper material provided with said device (as well as an assembly device employed in such a funerary container) that has reduced production costs.

DISCLOSURE OF THE INVENTION

The technical task set out above and the specified aims are substantially achieved by a funerary container made of plastic material provided with said device, as well as by the assembly device employed in said funerary container, having the characteristics set out in one or more of the accompanying claims.

DESCRIPTION OF THE DRAWINGS

The description is now provided, purely by way of non limiting example, of a preferred, but not exclusive, embodiment of a funerary container made of paper material and of an assembly device employed in said funerary container according to the invention, illustrated in the accompanying drawings, in which:

FIG. 6 shows a lateral view of an embodiment variation of the container according to the present invention; and FIG. 7 shows a front view of the embodiment variation of the container of FIG. 6.

DESCRIPTION OF THE ILLUSTRATIVE EMBODIMENTS

With reference to the aforesaid figures, the funerary container according to the invention is globally indicated with number 1.

It substantially comprises a predetermined number of laminar elements 2, which are flexibly connected to each other. Said laminar elements are made of cardboard with corrugated core (which can advantageously be obtained by recycling waste paper) and, in particular, according to loading requirements, can be constituted by multiple cardboard layers superposed on each other (in an arrangement that is practically similar to that of plywood).

The laminar elements 2 are mutually connected in such a way as to define, in mutual co-operation, a housing box body 3, which shall obviously serve the purpose of containing a body (or, rather, a human or animal corpse). Advantageously, said housing box body 3 has a bottom wall, a plurality of lateral walls and at least a closure portion (which in practice serves as a lid).

The laminar elements are obtained, in accordance with the prior art, by appropriately die cutting a blank made of more or less layered cardboard; advantageously, the profile of such die cutting shall substantially correspond to the development of the surface that delimits the housing box body 3.

Figure 2:
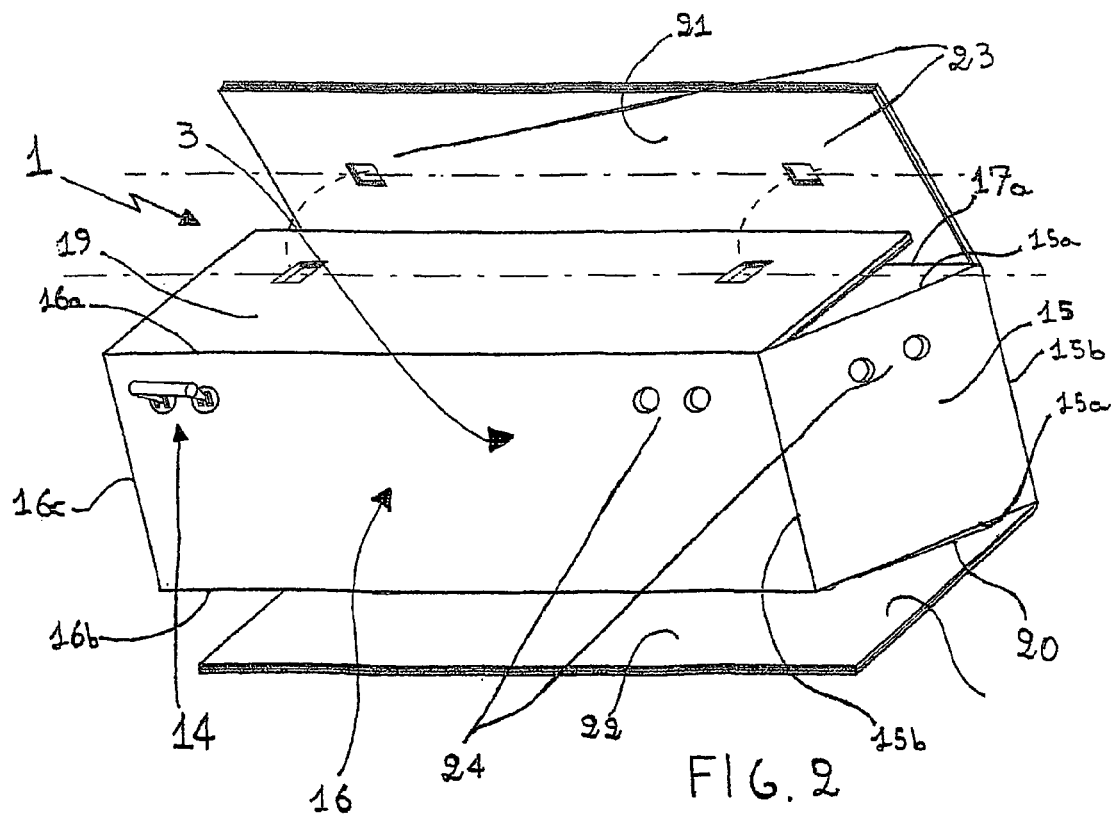
FIG. 2 shows a perspective view of the funerary container according to the present invention.

Delving deeper in the details, FIG. 2 shows that said laminar elements 2 comprise first of all a first head face 15, which has two primary folding sides 15*a* and two shared sides 15*b* positioned transversely relative to the primary folding sides 15*a* (in other words the first head face 15 is substantially a rectangle or a square, whose pairs of opposite sides respectively comprise the two primary folding sides 15*a* and the two shared sides 15*b*). Next to the first head face 15, there are a first and a second lateral faces 16, 17, respectively connected to the first head face 15 on each of the shared sides 15*b*; the first and the second lateral face exhibit respectively an upper long side 16*a*, 17*a*, a lower long side 16*b*, 17*b*, and a short side 16*c*, 17*c* opposite to one of the shared sides 15*b*.

In accordance with the present invention, a second head face 18 (substantially identical to the first head face 15) is present and connected to the first lateral face 16 or to the second lateral face 17 through one of the respective short sides 16*c* or 17*c*. Obviously, the second head face 18 also has two secondary folding sides (18*a*) positioned transversely relative to the short sides 16*c* or 17*c* (as the case may be).

The two head faces 15 and 8 and the two lateral faces 16 and 17 define the lateral walls of the housing box body 3.

Advantageously, a first upper closure face 19 is also present, connected to the first lateral face 16 through the upper long side 16*a*; in parallel, the presence is provided of a first lower closure face 20, connected to the first lateral face 16 through the lower long side 16*b*.

Conveniently, a second upper closure face 21 is lastly present, connected to the second lateral face 17 through the upper long side 17*a*; said second upper closure face 21 is flanked by a second lower closure face 22, which is connected to the second lateral face 17 through the lower long side 17*b*.

The four lower and upper closure faces define respectively the bottom and the closure portion of the housing box body 3.

An embodiment variation of the container 1 according to the present invention conveniently provides for the presence of some additional laminar elements 2; said laminar elements 2 find particular application when a container 1 characterised by a high rigidity of its vertices is to be obtained.

In accordance with said embodiment variation, one can observe, in FIG. 6, the presence of a first upper stiffening face 25 and of a first lower stiffening face 26, which are connected to the first head face (15) respectively through one of the primary folding sides (15*a*). In parallel, there are also a second upper stiffening face 27 and a second lower stiffening face 28; said faces are connected to the second head face 18 respectively through one of the secondary folding sides (18*a*).

Advantageously, the funerary container 1 according to the present invention further comprises a predetermined number of assembly devices 4; each of said assembly devices 4 is operatively active on at least two laminar elements 2 to keep them in a mutually approached position in operative conditions (in other words, the assembly device serve to maintain the shape of the housing box body 3 once the various laminar elements have been appropriately folded and mutually approached in such a way as to define it). It should be noted that the assembly devices 4 according to the present invention are designed in such a way as to assure a stable coupling between two due laminar elements (which, for the sake of descriptive consistency, we shall hereinafter define as a first laminar element 2*a* and a second laminar element 2*b*) constituting the container 1; in any case, should the needs of the case so require, it is possible for a single assembly device 4 to interconnect more than a pair of laminar elements 2 (for instance, if it should become necessary to add an additional cardboard panel to increase the ability to withstand the weight of the body to be transported or if the stiffening faces 25, 26, 27 and 28 are present; in this case, each assembly device will engage three laminar elements, i.e. two lower or upper closure faces and a stiffening face).

In accordance with the present invention, at least one (more in particular, all) of the assembly devices 4 comprises (comprise) essentially a main fastening element 5, which is irremovably connected to a first laminar element 2*a* and destined to receive in coupling fashion at least a second laminar element 2*b*.

In order further to improve the stability of the connection between the two laminar elements, the assembly device 4 further comprises a complementary fastening element 6; said complementary fastening element 6 is operatively active on the second laminar element 2*b* in operative conditions, and it is destined to be engaged at least partially on the main fastening element 5.

Advantageously, both the main fastening element 5 and the complementary fastening element 6 can easily be obtained from plastic material (for instance by moulding); it is also possible, in accordance with the present invention, to select a biodegradable plastic material, in order substantially to solve environmental impact problems deriving from a long term burial (or a cremation) of the subject container 1.

Figure 1:
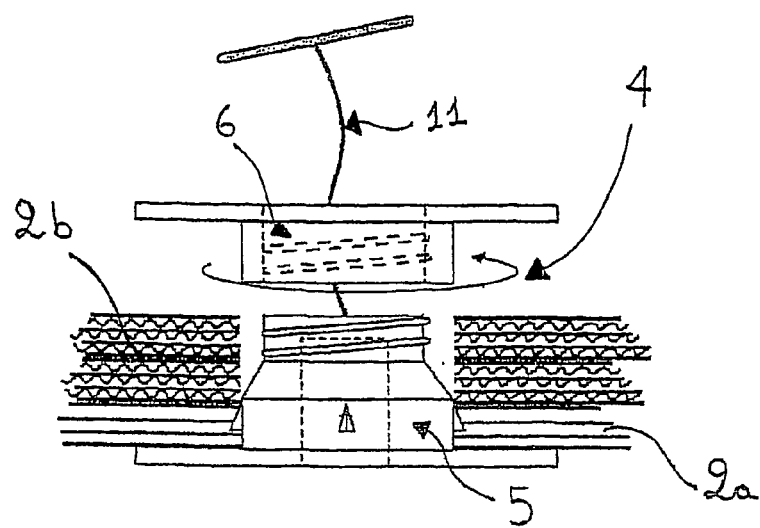
FIG. 1 shows a partial section view of the assembly device according to the present invention.

Delving deeper into details (see also FIGS. 1 and 3), one can observe that the main fastening element 5 comprises a main abutment portion 5a (for instance shaped in the manner of an annulus), which is destined to be engaged adjacently to a first side of the first laminar element 2a (which generally is an interior side of the housing box body 3). Also present is a main active portion 5b, which extends towards a second side of the first laminar element 2a opposite the first side (typically, the exterior side).

Conveniently, the main active portion 5b is substantially shaped according to a prismatic body having its axis of development substantially transverse (in practice, perpendicular) to the plane of lay of the first laminar element 2a.

Analysing the figures, one also notes that said prismatic body comprises a locking body 7, obtained laterally on the prismatic body and destined to be irremovably engaged with the first laminar element 2a in operative conditions; in other words, the locking body 7 directly realises the condition of irremovable coupling between the main fastening element 5 and the first laminar element 2a.

In practice, the realisation of an irremovable coupling is guaranteed by the particular conformation of the locking body 7 itself, since it is substantially shaped as a retaining tooth.

In particular, the locking body 7 has an insertion surface 7a (oriented according to a predetermined insertion angle 8 relative to the longitudinal axis of development of the prismatic body) and an abutment surface 7b connected to the insertion surface 7a (which instead is oriented along a direction perpendicular to the longitudinal axis of development of the prismatic body).

During the assembly of the container 1, the operator forces the cylindrical body through appropriate openings (which in practice are the housing seats 23 described farther on) obtained in the first laminar element 2a; the locking body 7 is thereby progressively inserted inside the cardboard, in such a way as to make its accidental release nearly impossible.

Figure 3:
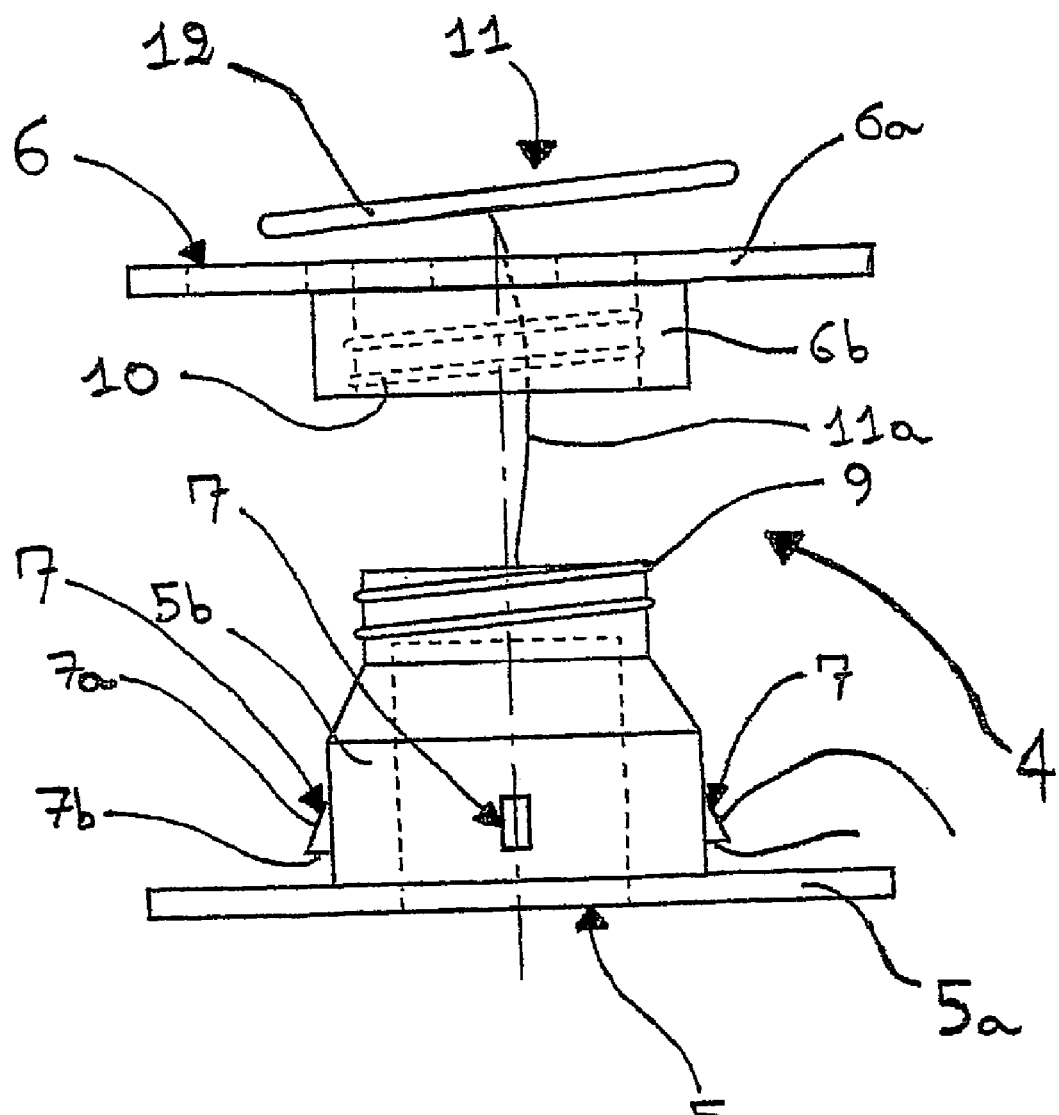
FIG. 3 shows a lateral view of the assembly device of FIG. 1.
Figure 4:
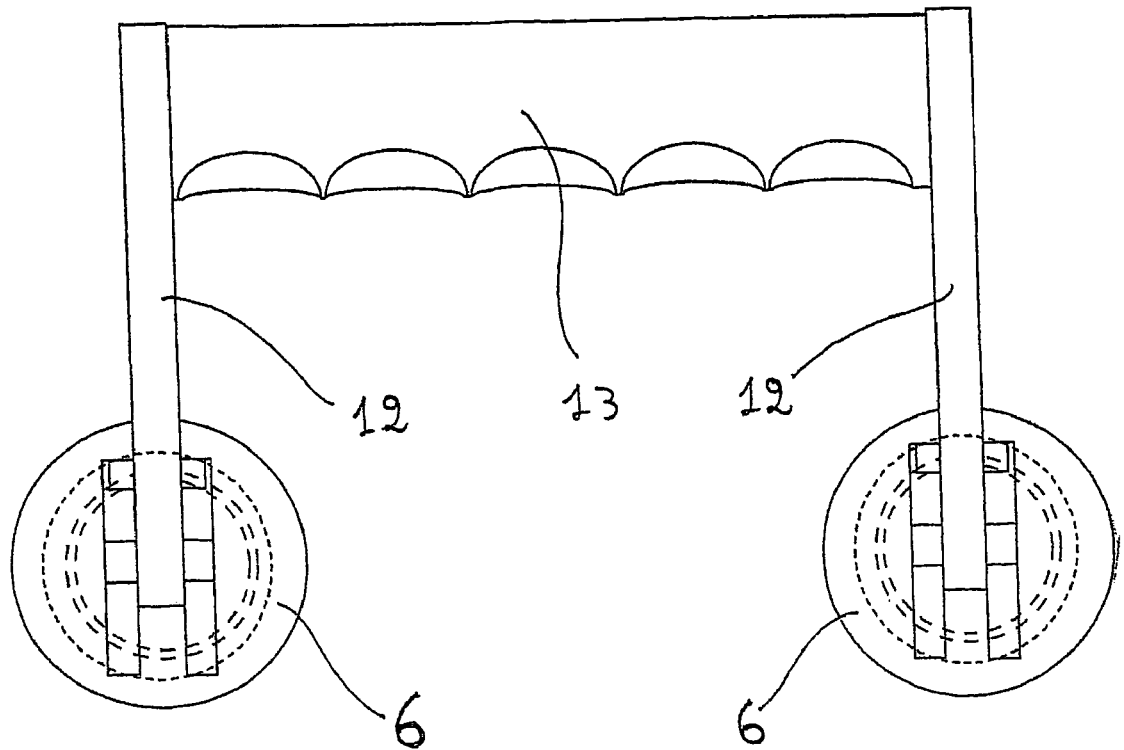
FIG. 4 shows a front view of an embodiment variation of the assembly device of FIG. 1.
Figure 5:
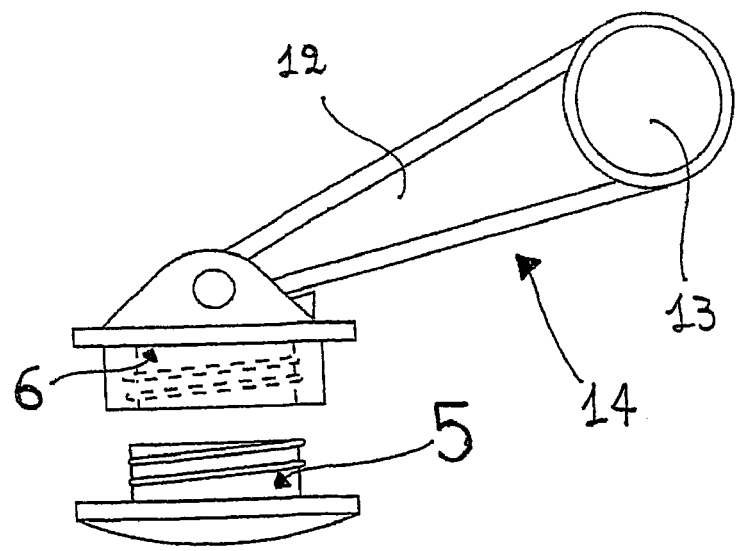
FIG. 5 shows a front view of the embodiment variation of the assembly device of FIG. 4.

Advantageously, to obtain the utmost behavioural symmetry, the main active portion 5b comprises a predetermined number of locking bodies 7 spaced at equal radial intervals on the prismatic body and positioned at a predetermined distance from the abutment portion 5a (in FIG. 3, for instance, one notes four locking bodies 7 set 90° from each other and all positioned at the same height relative to the abutment portion 5a).

Advantageously, the main active portion 5b further comprises mechanical fastening means, which are obtained on the and are destined to be engaged with the fastening element 6 in operative conditions. In particular, said mechanical fastening means comprise a thread 9, which extends laterally from the prismatic body and operates in ways that shall be explained in greater detail farther on.

In accordance with the present invention, the complementary fastening element 6 comprises (similarly to the main fastening element 5) a complementary abutment portion 6a, destined to be engaged adjacently to a first surface of the second laminar element 2b, and a complementary active portion 6b extending towards a second surface of the second laminar element 2b (typically, towards the interior of the housing box body 3). At this point it should be specified that, in operative conditions (i.e. when the container 1 is completely mounted), the aforesaid second surface of the second laminar element 2b is practically opposite to the first surface of the second laminar element 2b; obviously, the second surface of the second laminar element 2b and the second side of the first laminar element 2a being in mutual contact in operative conditions.

The complementary active portion 6b conveniently comprises interconnection means destined to engage the mechanical fastening means of the main active portion 5b; in particular, said interconnection means comprise a hollow prismatic body extending from the complementary abutment portion 6a and having in its interior a helical groove 10 substantially counter-shaped relative to the thread 9.

When performing the operations for mounting the container 1, the operator, after inserting the main fastening element 5 in irremovable fashion in the first laminar element 2a and after approaching the first laminar element 2a itself to the second laminar element 2b, mutually engages the main fastening element 5 to the complementary fastening element 6, typically by meshing the thread 9 with the helical groove 10.

To facilitate the approach of the first laminar element 2a and of the second laminar element 2b, guide means 11 are advantageously present, which are connected to the main fastening element 5.

Said guide means 11 are operatively active on the main fastening element 5 to determine, or in other words to facilitate, the approach of the first laminar element 2a to the second laminar element 2b.

The guide means 11 substantially comprise a traction body 11a connected to the main active portion 5b; said traction element 11a is conveniently actuated by an operator (when mounting the container 1) to approach the first laminar element 2a to the second laminar element 2b; in other words, the operator, after inserting the main the fastening element 5 pulls it towards the exterior by means of the traction body 11a, to approach all components constituting the container to be assembled.

In a preferred embodiment, the traction body 11a is simply a thread-like element, having a first end connected to the main abutment portion 5a and a second end (opposite to the first end) provided with an actuation interface 12 (typically, a body of any shape provided it is suitable for being gripped and handled by an operator in operative conditions).

An advantageous embodiment variation relating to the traction body 11a provides for said traction body to be a rigid element 12; said rigid element 12 has a first end hinged to the complementary abutment portion 6a (for instance according to a hinge axis that is substantially parallel to the plane of lay of the second laminar element 2b) and a second end opposite to the first end. On the second end of the rigid element 12 is present a contoured grip 13 (which can properly be defined a handle) destined to be gripped by a hand of the user. The presence of such a rigid element 12 finds useful application if the container 1 is to be provided with a series of transport handles; in this case, the container 1 itself comprises a predetermined number of coupled assembly devices 14 (mounted on the laminar elements defining the lateral walls of the housing box body 3), each of which has at least two main fastening elements 5 (connected to a first laminar element 2a, mutually distanced by a predetermined interval and advantageously destined to receiving in coupling fashion at least a second laminar element 2, preferably one for each of the two elements 5).

Advantageously, to said pair of main fastening elements 5 are associated (when the container 1 is assembled) two complementary fastening elements 6, each of which respectively engages the main fastening elements 5 and equally provided with two rigid elements 12, which in turn have their ends hinged respectively to complementary tightening elements 6 and their second ends mutually connected by a grip 13.

In this case, the grip 13 extends between the rigid elements 12 for a length substantially corresponding to the aforesaid spacing, in such a way as to define a large handle which is so positioned as to allow an operator easily to lift the container 1 whilst standing to its side.

Conveniently, the container according to the present invention further comprises a predetermined number of housing seats 23 (obviously obtained in the manner best suited to the requirements of the moment on the different laminar elements 2), each of which is destined to receive an assembly device 4.

As the accompanying figures show, the housing seats 23 are obtained at least on the first lower closure face 20 and on the second lower closure face 22 (in such a way as to define the bottom of the housing box body 3); obviously, said housing seats 23 are in substantially corresponding positions in operative conditions. In order to close the container conveniently after placing therein the body to be transported or buried, the housing seats 23 are also obtained on the first upper closure face 19 and on the second upper closure face 21 (also in substantially corresponding positions in operative conditions); in this way the assembly of the container is complete, i.e. it is possible to define also the closure portion of the container 1 itself.

In the particular embodiment variation of the container 1 that provides for the presence of the stiffening faces 25, 26, 27 and 28, naturally the housing seats 23 are also obtained on the first lower stiffening face 26, on the second lower stiffening face 28, on the first upper stiffening face 25 and on the second lower stiffening face 28.

Conveniently, said housing seats 23 shall be placed in substantially corresponding positions in operative conditions.

Naturally, to facilitate the mounting of the container 1 to the maximum possible extent, the latter housing seats shall be placed in positions corresponding to the housing seats 23 obtained respectively on the first lower closure face 20 and/or on the second lower closure face 22 and/or on the first upper closure face 19 and/or on the second upper closure face 21; in this way the assembly devices interconnect as many as three laminar elements, once they are duly installed in the housing seats 23 (which will simultaneously be superposed).

Lastly, it should be noted that the container according to the present invention further comprises a predetermined number of securing seats 24 (obtained in the first head face 15 and/or in the first lateral face 16 and/or in the second lateral face 17 and/or in the second head face 18, depending on requirements of maximum transportable weight or ease of transport of the loaded container); said securing seats, which are essentially constituted by a pair of through holes, serve essentially to house the coupled assembly devices 14.

The invention achieves important advantages.

First of all, it should be noted that the disposition of the two main elements constituting the assembly device allows an effective connection between two or more laminar elements (which concur to define a pair of walls of the funerary container itself); in particular, it should be remarked that the assembly device according to the present invention allows to avoid harmful areas where stresses accumulate, preventing the occurrence of crushing or lacerations in the cardboard and consequently maintaining unaltered the shape and integrity of the container.

Another typical advantage of such an assembly device consists of the fact that its main components can be effectively inserted in the laminar cardboard elements in a secure manner and with a minimum series of adaptation operations, to the advantage of the reduction in production times and costs (as well as ease of construction).

Lastly, the subject device allows considerably to simplify the assembly of the container at the time it is needed, since it allows the operator to approach, effectively and precisely, the laminar cardboard elements and subsequently to obtain a mechanical coupling with few, very simple operations.

It should also be stressed that the present assembly device exhibits very reduced exterior dimensions and is suitable for being placed in any position on the outer surface of the container 1; this entails advantages also in terms of stowage ease, since it is possible to keep the assembly devices and the cardboard elements separate until the time of need, then installing the assembly devices simply by means of inserting them in snap-on fashion on the cardboard elements.

Another advantage of the present invention is provided by the extreme simplicity of shape of the container, which additionally allows for a very high load bearing capacity without making use of a stiffening frame; in connection thereto, one should lastly note the characteristic of the funerary container according to the present invention whereby it exhibits an extremely low environmental impact; this is essentially due to the large percentage of recycled material that can be employed, coupled also to the absence of poorly biodegradable materials or of materials able to produce harmful waste if subjected to cremation.

Lastly, it should be stressed that the funerary container made of paper material and the assembly device reduce production costs and considerably simplify fabrication processes.

What is claimed is:

1. Assembly device, for containers made of paper material, comprising:
   a main fastening element (5) irremovably connectable to a first laminar element (2a), said first laminar element (2a) being an interior side of the container (1) and allowing the coupling of said first laminar element (2a) with at least a second laminar element (2b) of the container (1), said second laminar element (2b) being an exterior side of the container (1);
   a complementary fastening element (6) activable on the second laminar element (2b) in operative conditions and destined to engage at least partially with the main fastening element (5);
   a main active portion (5b) of the main fastening element (5), said main active portion (5b) presenting mechanical fastening means extending towards the exterior side of the container (1) in assembling conditions and destined to engage with the complementary fastening element (6), said mechanical fastening means comprising a thread (9), said main active portion (5b) being shaped according to a prismatic body having a longitudinal axis transverse to the plane of lay of the first laminar element (2a), said prismatic body comprising at least a locking body (7) extending outwardly from said prismatic body and destined to be irremovably engaged with the first laminar element (2a) in operative conditions; and a complementary active portion (6b) of the complementary fastening element (6), the complementary active portion presenting interconnection means extending towards the interior side of the container (1) in assembling conditions and destined to engage the mechanical fastening means of the main active portion (5b), said interconnection means comprising a hollow prismatic body having in its interior a helical groove (10) counter shaped relative to the thread (9).

2. Assembly device as in claim 1, further comprising a main abutment portion (5a) of the main fastening element destined to be engaged adjacently to a first face of the first laminar element (2a).

3. Assembly device as in claim 1, wherein said locking body (7) has an insertion surface (7a) oriented according to a predetermined insertion angle (8) relative to the longitudinal axis of the prismatic body and an abutment surface (7b) connected to said first insertion surface (7a) and oriented along a direction perpendicular to the longitudinal axis of the prismatic body.

4. Assembly device as in claim 1, wherein the main active portion (5b) comprises a predetermined number of the locking bodies (7) radially set at equal distances on the prismatic body and placed at a predetermined distance from an abutment portion (5a) of the main fastening element.

5. Assembly device as in claim 4, wherein said thread (9) is extending laterally from said prismatic body.

6. Assembly device as in claim 1, wherein the complementary fastening element (6) comprises a complementary abutment portion (6a) destined to engage adjacently with a first surface of the second laminar element (2b).

7. Assembly device as in claim 1, further comprising guide means (11) connected to the main fastening element (5) and operatively active thereon to determine an approach of the first laminar element (2a) to the second laminar element (2b).

8. Assembly device as in claim 7, wherein said guide means comprise a traction body (11a) connected to the main active portion (5b) and destined to be actuated by an operator to approach the first laminar element (2a) to the second laminar element (2b).

9. Assembly device as in claim 8, wherein said traction body (11a) is a thread element having a first end connected to the main active portion (5b) and a second end opposite to said first end and presenting an actuation interface (12) destined to be handled by the operator in operative conditions.

10. Assembly device as in claim 8, wherein the traction body (11a) is a rigid element (12) having a first end hinged to a complementary abutment portion (6a) of the complementary fastening element according to a hinge axis that is parallel to the plane of lay of the second laminar element (2b) and a second end opposite to the first end and having a contoured grip (13) destined to be gripped by the users hand.

11. Assembly device as in claim 1, further comprising a predetermined number of coupled assembly devices (14), each of which has:

at least two said main fastening elements (5) connected to the first laminar element (2a) and mutually distanced by a predetermined spacing and destined to receive in coupling fashion the second laminar element (2b);

at least two said complementary fastening elements (6) respectively engaging the main fastening elements (5); and at least two rigid elements (12) having first ends hinged respectively to the complementary fastening elements (6) and second ends mutually connected by a grip (13), said grip (13) extending between the rigid elements (12) for a length corresponding to said spacing.

12. Funerary container made of paper material, comprising:

a predetermined number of laminar elements (2) flexibly connected to each other and defining, in mutual co-operation, a housing box body (3) destined to contain a body and having at least a bottom wall, a plurality of lateral walls and at least a closure portion; and a predetermined number of assembly devices (4), whereof each is operatively active on at least two said laminar elements (2) to keep them in a mutually approached position in operative conditions, at least one of said assembling devices (4) comprising:

a main fastening element (5) irremovably connectable to a first said laminar element (2a), said first laminar element (2a) being an interior side of said container (1) and allowing the coupling of said first laminar element (2a) with at least a second said laminar element (2b) of the container (1), said second laminar element (2b) being an exterior side of the container (1);

a complementary fastening element (6) activable on the second laminar element (2b) in operative conditions and destined to engage at least partially with the main fastening element (5);

a main active portion (5b) of the main fastening element (5), said main active portion (5b) presenting mechanical fastening means extending towards the exterior side of the container (1) in assembling conditions and destined to engage with the complementary fastening element (6), said mechanical fastening means comprising a thread (9), said main active portion (5b) being shaped according to a prismatic body having a longitudinal axis transverse to the plane of lay of the first laminar element (2a), said prismatic body comprising at least a locking body (7) extending outwardly from said prismatic body and destined to be irremovably engaged with the first laminar element (2a) in operative conditions; and a complementary active portion (6b) of the complementary fastening element (6), said complementary active portion presenting interconnection means extending towards the interior side of the container (1) in assembling conditions and destined to engage the mechanical fastening means of the main active portion (5b), said interconnection means comprising a hollow prismatic body having in its interior a helical groove (10) counter shaped relative to the thread (9).

13. Container as in claim 12, wherein said predetermined number of laminar elements (2) comprises:

a first head face (15) having two primary folding sides (15a) and two shared sides (15b) positioned transversely relative to said primary folding sides (15a);

a first and a second lateral faces (16, 17) connected to said first head face (15) through each of said shared sides (15b), said first and said second lateral faces having each an upper long side (16a, 17a), a lower long side (16b, 17b) and a short side (16c, 17c) opposite to one of said shared sides (15b);

a second head face (18) substantially identical to the first head face (15) and connected to the first lateral face (16) or to the second lateral face (17) through said short side (16*c*) or (17*c*), said second head face (18) presenting two secondary folding sides (18*a*) positioned transversely relative to the short side (16*c*) or (17*c*);

a first upper closure face (19) connected to the first lateral face (16) through said upper long side (16*a*);

a first lower closure face (20) connected to the first lateral face (16) through said lower long side (16*b*);

a second upper closure face (21) connected to the second lateral face (17) through said upper long side (17*a*); and a second lower closure face (22) connected to the second lateral face (17) through said lower long side (17*b*).

14. Container as in claim 13, further comprising:

a first upper stiffening face (25) and a first lower stiffening face (26) connected to the first head face (15) respectively through one of the primary folding sides (15*a*); and a second upper stiffening face (27) and a second lower stiffening face (28) connected to the second head face (18) respectively through one of the secondary folding sides (18*a*).

15. Container as in claim 12, wherein the predetermined number of laminar elements (2) further comprises a predetermined number of housing seats (23) each destined to receive the assembly device (4).

16. Container as in claim 15, wherein said housing seats (23) are obtained at least on a first lower closure face (20) and on a second lower closure face (22) in corresponding positions in operative conditions, the housing seats (23) being obtained also on a first upper closure face (19) and on a second upper closure face (21) in corresponding positions in operative conditions.

17. Container as in claim 16, wherein the housing seats (23) are obtained at least on a first lower stiffening face (26) and on a second lower stiffening face (28), the housing seats (23) being obtained also on a first upper stiffening face (25) and on a second lower stiffening face (28) in corresponding positions in operative conditions and in positions corresponding to the housing seats (23) obtained on the first lower closure face (20) and/or on the second lower closure face (22) and/or on the first upper closure face (19) and/or on the second upper closure face (21).

18. Container as in claim 12, further comprising a predetermined number of securing seats (24) obtained in a first head face (15) and/or in a first lateral face (16) and/or in a second lateral face (17) and/or in a second head face (18) to house said predetermined number of coupled assembly devices (14).

19. Container as in claim 12, wherein the main active portion (5*b*) comprises a predetermined number of the locking bodies (7) radially set at equal distances on the prismatic body and placed at a predetermined distance from an abutment portion (5*a*) of the main fastening element.

20. Container as in claim 19, wherein said thread (9) is extending laterally from said prismatic body.

* * * * *